(12) United States Patent
Engström et al.

(10) Patent No.: US 7,168,855 B2
(45) Date of Patent: Jan. 30, 2007

(54) X-RAY STAND

(75) Inventors: Göran Engström, Johanneshov (SE); Mikael Lundberg, Upplands Väsby (SE); Erik Mellström, Järfälla (SE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/536,761

(22) PCT Filed: Oct. 31, 2003

(86) PCT No.: PCT/EP03/12156

§ 371 (c)(1),
(2), (4) Date: Mar. 2, 2006

(87) PCT Pub. No.: WO2004/047644

PCT Pub. Date: Jun. 10, 2004

(65) Prior Publication Data

US 2006/0153340 A1    Jul. 13, 2006

(30) Foreign Application Priority Data

Nov. 28, 2002    (SE) ................................ 0203517-8

(51) Int. Cl.
*H05G 1/02* (2006.01)

(52) U.S. Cl. ...................................... 378/197; 378/196
(58) Field of Classification Search ......... 378/193–198
See application file for complete search history.

(56) References Cited

U.S. PATENT DOCUMENTS

| 5,155,757 A * | 10/1992 | Sakaniwa et al. ........... 378/197 |
| 5,410,584 A | 4/1995 | Schaefer et al. |
| 6,428,206 B1 * | 8/2002 | Watanabe .................... 378/197 |

\* cited by examiner

*Primary Examiner*—Courtney Thomas
*Assistant Examiner*—Hoon Song

(57) ABSTRACT

The invention relates to an X-ray stand comprising an outer C arm along which a support for an inner C arm is displaceably mounted. The inner C arm which carries an X-ray tube and an image intensifier is displaceably arranged in the support. The X-ray stand further comprises a drive device for the displacement of the support along the outer C arm and the displacement of the inner C arm along the support. The aim of the invention is to create an X-ray stand of the above-described kind that comprises a drive device that is relatively inexpensive, requires little space and allows for a relatively high positioning accuracy. This aim is achieved in that the drive device is provided with a single drive means that influences the inner C arm and the support simultaneously in such a manner that the inner C arm and the support move in the same direction.

9 Claims, 4 Drawing Sheets

X-RAY STAND

CROSS REFERENCE TO RELATED APPLICATIONS

This application claims priority to the Swedish application No. 0203517-8, filed Nov. 28, 2002 and to the International Application No. PCT/EP03/12156, filed Oct. 31, 2003 which are incorporated by reference herein in their entirety.

FIELD OF INVENTION

The invention relates to an X-ray stand comprising an outer C arm along which a support for an inner C arm is displaceably mounted, the inner C arm, which carries an X-ray tube and an image intensifier, being displaceably arranged in the support, and a drive device for the displacement of the support along the outer C arm and for the displacement of the inner C arm along the support.

BACKGROUND OF INVENTION

An X-ray stand of the aforementioned type is shown and described in U.S. Pat. No. 5,410,584. The drive device of this X-ray stand comprises two motors, the one motor being provided in order to displace the support along the outer C arm and the other motor being provided in order to displace the inner C arm along the support. An X-ray stand of this type allows orbital displacements of approximately ±100°. In connection with such large orbital displacements, it can be difficult with a drive device consisting of multiple motors to achieve a steady movement of the inner C arm and a desired positioning accuracy without a complicated control-engineering solution. A drive device of this kind is therefore frequently expensive and needs a large amount of space.

From U.S. Pat. No. 6,428,206 an X-ray diagnostic apparatus is known in which the X-ray generator and the X-ray detector are held on a semi-circular C arm. The X-ray generator is connected by means of a first linear motor to a first quadrantal arm which for its part is movably held with a second arm by means of a second linear motor. By means of a third motor, this second arm is movable independently of the other motors. The support base is mounted on the floor, on a wall or on the ceiling. Here, too, the X-ray diagnostic apparatus has multiple motors for orbital displacement which, for accurate positioning, particularly in the case of the imaging technology described in U.S. Pat. No. 6,428,206, requires very accurate and synchronized control from a large number of possible positions.

SUMMARY OF INVENTION

An object of the invention is to create an X-ray stand of the kind specified in the introduction comprising a drive device which is relatively inexpensive and requires little space and with the aid of which a relatively high positioning accuracy can be achieved.

This object is achieved by the claims. The drive means is preferably a motor. Due to the fact that only one motor is to be controlled, the drive is simple to construct and therefore inexpensive. It is also easy to adjust. The positioning accuracy can then be brought to a high level by means of a relatively simple control-engineering arrangement. The space for the drive device can be kept relatively small, on account of the simple construction of the device.

The drive device according to the invention is preferably arranged in the support.

According to the invention, the drive device influences the inner C arm and the support respectively by a gear ratio, the gear ratios being in the same ratio to one another as the lengths of the two C arms. Depending on the choice of gear ratios, the lengths of the outer C arm and of the inner C arm can be chosen such that a desired optimal length of telescopic movement of the C arms in an X-ray stand of the aforementioned kind is obtained.

In a relatively simple embodiment of the drive device according to the invention it is proposed that the gear ratio be effected via a gear drive.

In an advantageous further development of the drive device according to the invention it is proposed that the drive means displace the inner C arm with the aid of a first belt transmission and drive a coupling wheel via a coupling transmission, said coupling wheel for its part displacing the support via a second belt transmission, whereby the ends of the belt of the first belt transmission are fastened to the inner C arm and the ends of the belt of the second belt transmission are fastened to the outer C arm.

This construction of the drive device ensures a relatively vibration-free and thus steady movement of the C arm, even where rapid C arm movements and long movement paths are involved.

The coupling transmission between the first and the second belt transmissions can be a drive belt or a roller chain. The coupling transmission can according to the invention also be a gear transmission.

As the drive device is mounted in the support, the outer C arm is preferably rotatably connected via a shaft to a stand arm. Consequently, the inner C arm can also be rotated with the support around the aforementioned shaft.

BRIEF DESCRIPTION OF THE DRAWINGS

The invention will be described in detail below with reference to an exemplary embodiment shown in the drawings, in which.

DETAILED DESCRIPTION OF INVENTION

Figure 1:
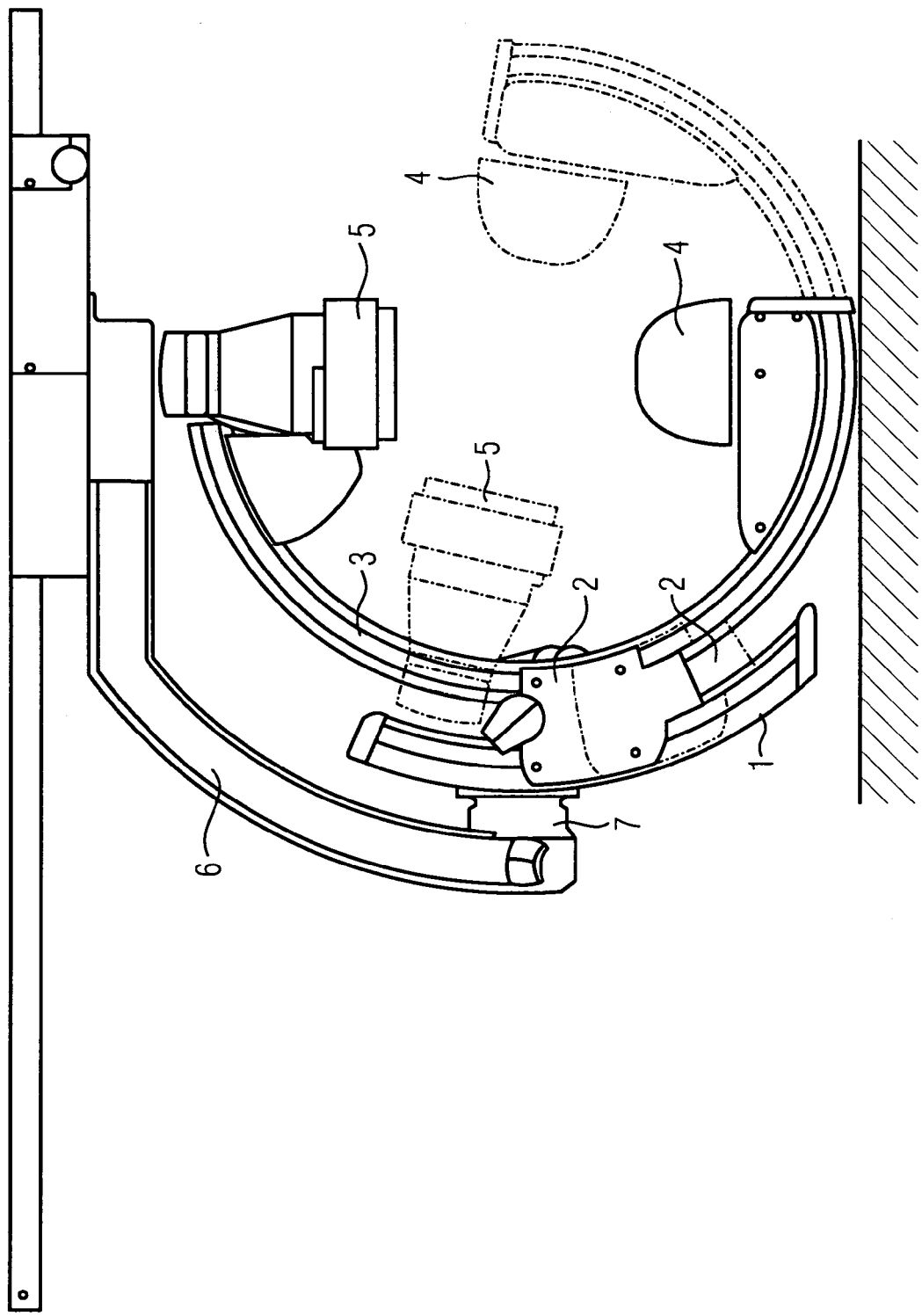
FIG. 1 shows a lateral view of an X-ray stand constructed in such a manner that a drive device according to the invention can be used.

FIG. 1 shows an X-ray stand hung from the ceiling, said X-ray stand comprising an outer C arm 1 along which a support 2 for an inner C arm 3 is displaceably mounted. The inner C arm 3, which carries an X-ray tube 4 and an image intensifier 5, is displaceably arranged in the support 2. A drive device, which is not shown in the drawing and which will be described in more detail later, for the displacement of the support 2 along the outer C arm 1 and for the displacement of the inner C arm 3 along the support 2 is arranged in the support 2. The outer C arm 1 and thus also the support 2 and the inner C arm 3 are rotatably connected via a shaft 7 to a stand arm 6 of the stand.

Figure 2:
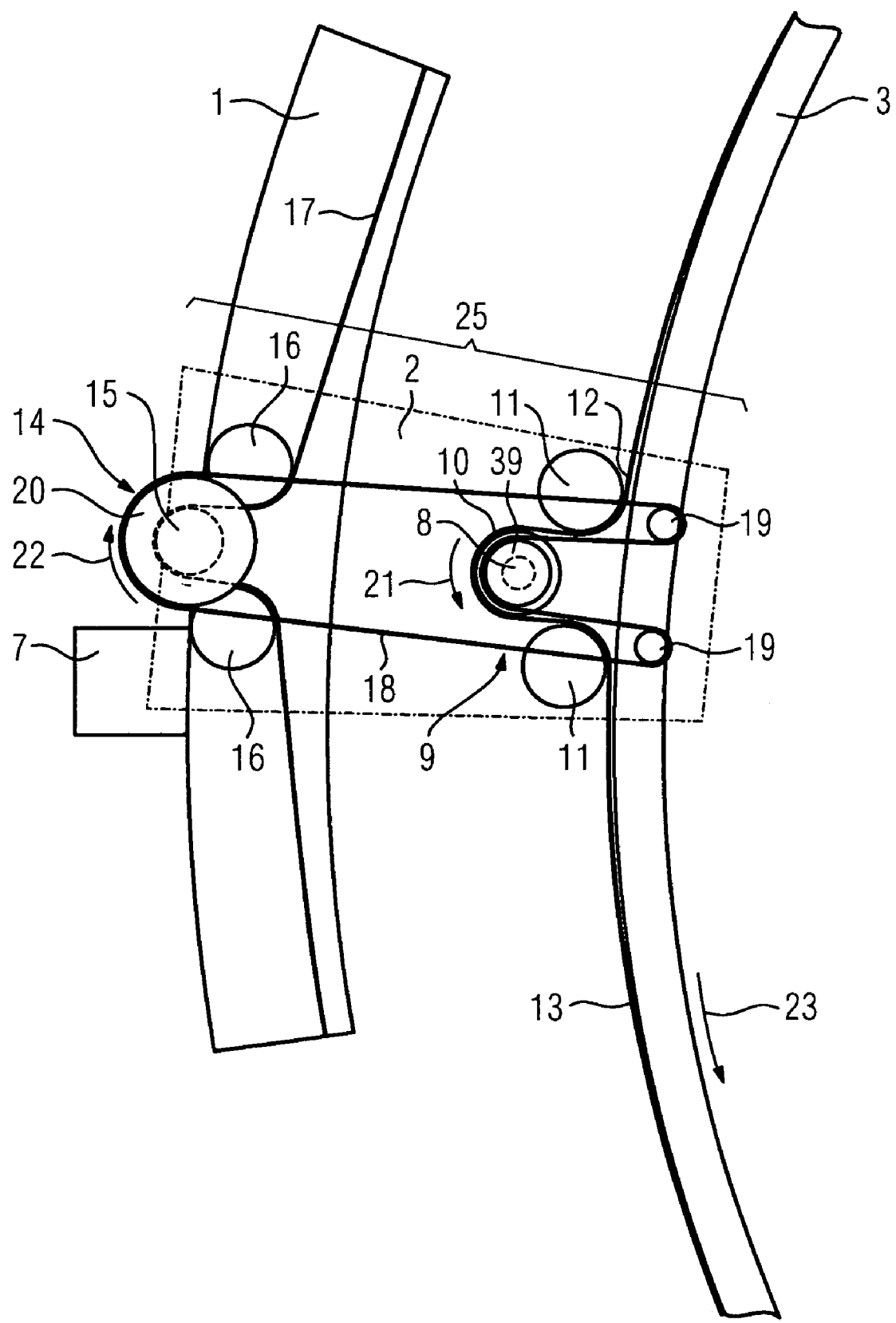
FIG. 2 shows a schematic construction of a drive device according to the invention.

FIG. 2 shows in schematic form a drive device 25. The drive device 25 comprises a single drive means in the form of a motor 8 and a first omega-shaped belt transmission 9, consisting of a wheel 10 which is driven with the aid of the motor 8, of two guide rollers 11 which are mounted on each side of the wheel 10, and of a toothed belt 12 which runs on the wheel 10, on the guide rollers 11 and along the back 13 of the inner C arm 3. The ends of the toothed belt 12 are fastened to the back 13 of the inner C arm 3. The drive device 25 comprises also a second omega-shaped belt transmission 14 comprising a wheel 15, two guide rollers 16 and a toothed belt 17, the ends of which are fastened to the outer C arm 1. The drive device 25 also has a coupling transmission 18, which connects the first and the second drive transmissions 9 and 14. The coupling transmission 18 consists here of an endless drive belt, which runs on the first belt transmission 9 on the wheel 39, said wheel being connected to the motor 8. The drive belt also runs over guide rollers 19, which are arranged next to the first belt transmission 9, to a wheel 20, which is arranged on the second belt transmission 14 and rigidly connected to the wheel 15. The belts 12, 17 and 18 can also be roller chains.

In connection with the driving of the inner C arm 3 in an orbital movement, the wheel 10 is rotated by the motor 8 e.g. in the direction of the arrow 21. The wheels 39 and 20, and thus also the wheel 15, are simultaneously rotated, with the aid of guide rollers 19 and the drive belts 18, in the direction of the arrow 22. The inner C arm 3 is then driven by the described configuration of the first belt transmission 9 in such a manner that it is displaced into the support 2 in the direction of the arrow 23 at the same time as the support 2 is driven by the described configuration of the second belt transmission 14 in such a manner that it is displaced, relative to the outer C arm 1 rigidly positioned in space, in the same direction as the inner C arm 3. The gear ratio of the coupling transmission is chosen by determining the size, i.e. the diameter, of the wheels 10 and 39 in relation to the diameter of the wheels 20 and 15.

A displacement of the C arm 3 in its longitudinal direction, a so-called orbital movement, is shown in the figure by means of dot-dash contours of the C arm 1, the X-ray tube 4 and the image intensifier 5.

In the event of the C arm moving in the opposing direction, the aforementioned wheels 20, 39 are rotated with the aid of the motor 8 in the opposing direction.

Figure 3:
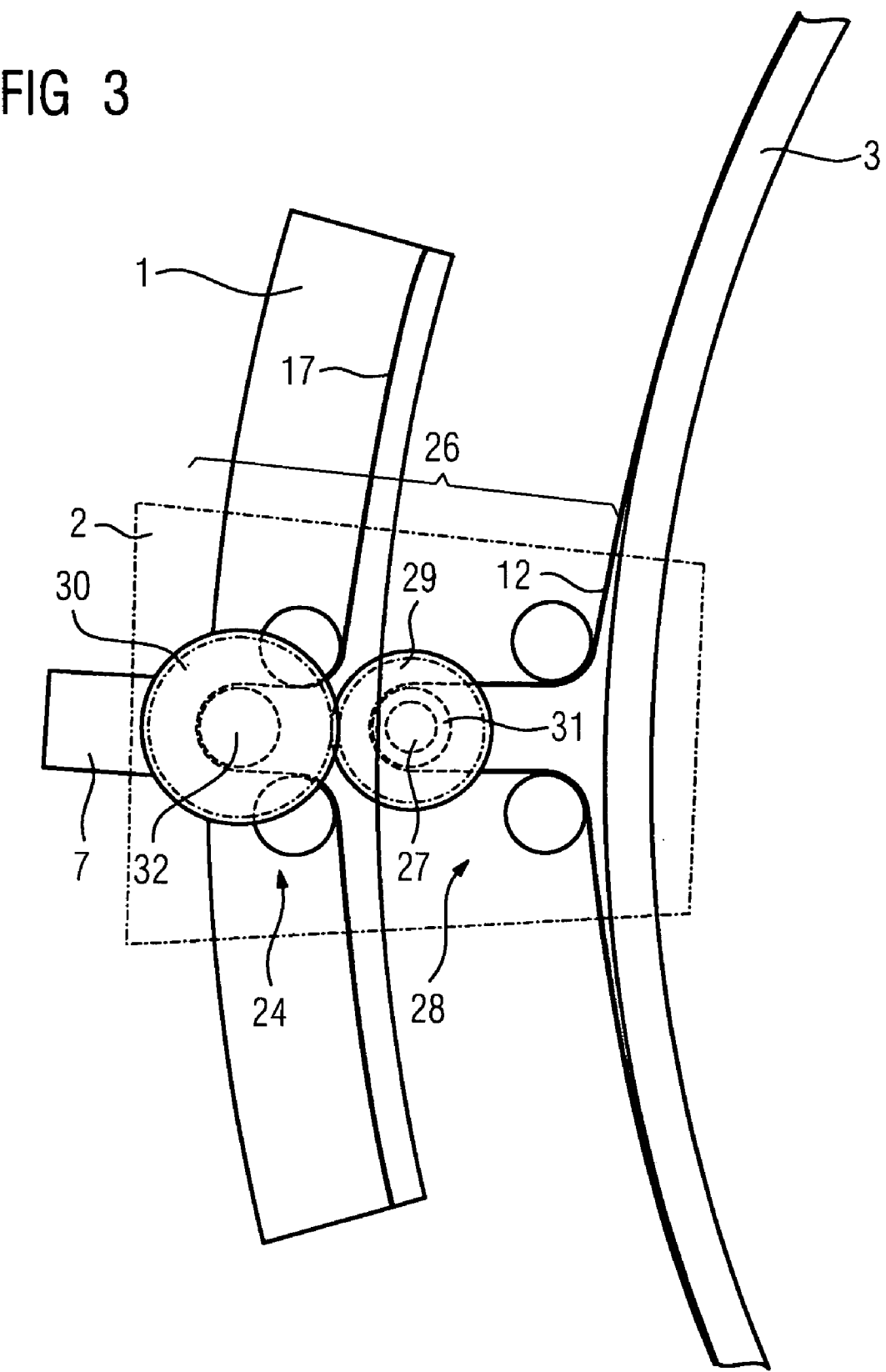
FIG. 3 shows a schematic construction of a second drive device according to the invention and FIG. 4 shows a schematic construction of a third drive device according to the invention.

FIG. 3 shows schematically a further drive device 26. The drive device 26 has the same structure as the drive device shown in connection with FIG. 2, i.e. with a first belt transmission 28 and a second belt transmission 24, the first belt transmission 28 being connected to a motor 27. In place of the drive belt 18 described in connection with FIG. 1, the coupling transmission in this drive device 26 consists of a gear transmission. The gear transmission has two gear wheels 29, 30 which are rigidly connected to the wheels 31, 32 for the two belt transmissions 28, 24 and the teeth of which are interlocking. If the wheel 31 is rotated with the aid of the motor 27, the gear wheel 29, and thus also the gear wheel 30, is also rotated, whereby a movement, described in detail in connection with the drive device 25 (FIG. 1), of the inner C arm 3 and of the support 2 occurs. The gear ratio of the coupling transmission is determined by the diameter of the gear wheels 29 and 31 relative to the diameter of the wheels 30 and 32.

Figure 4:
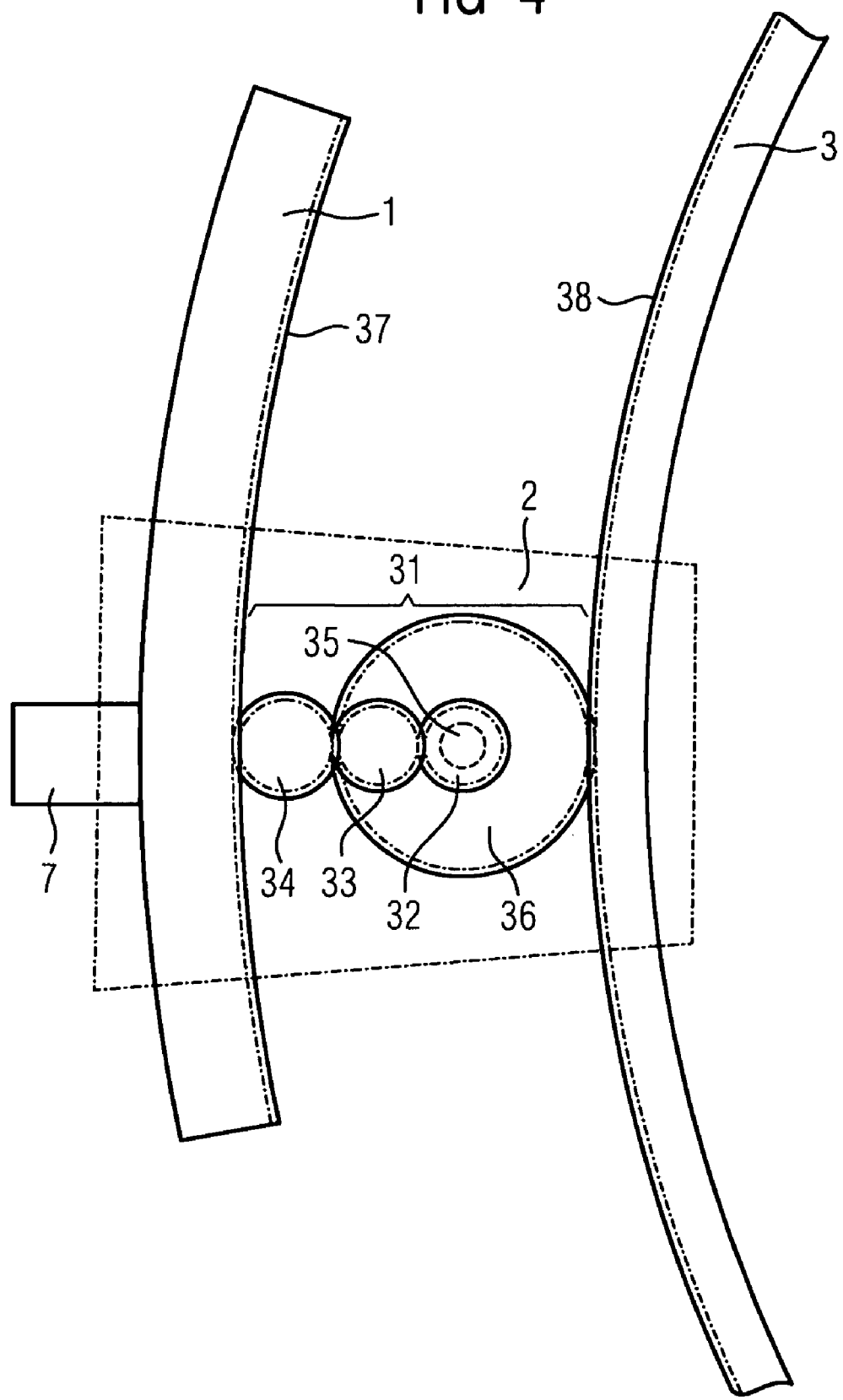

FIG. 4 shows schematically a further drive device 40, of a simplified form compared with the previously described drive devices 25, 26. The drive device 40 consists of a gear drive, so that a gear ratio is created between the outer and the inner C arm 1, 3. The gear drive comprises three adjacent gear wheels 32, 33, 34 the teeth of which are interlocking, the gear wheel 32 being connected to a motor 35. A gear wheel 36, said gear wheel being larger than the gear wheels 32, 33, 34, is rigidly connected to the gear wheel 32. The inside 37 of the outer C arm 1 and the back 38 on the inner C arm 3 are toothed. The gear wheel 36 of the drive device 40 can therefore displace the inner C arm 3 in the support 2 with the aid of the motor 35. The gear wheel 34 is simultaneously forced to move along the inside 37 of the outer C arm 1 in the same direction. The gear ratio here depends on the size difference between the gear wheels 36 and 32.

By means of the drive device according to the invention, the X-ray stand described can carry out large orbital movements steadily, at a high speed and with a high positioning accuracy. All this is of great significance, since it should be possible for a fairly large number of exposures to be carried out during the travel of the inner C arm.

The invention claimed is:

1. An X-ray stand, comprising:
 an outer C arm;
 a support for accomodating an inner C arm, the support displaceably arranged along the outer C arm, and the inner C-arm carrying an X-ray tube and an image enhancer, the inner C arm displaceably arranged within the support; and
 a drive device for displacing the support along the outer C arm and for displacing the inner C arm along the support, wherein the drive device consists of a motor displaceably coupled to the inner C arm and the support for simultaneously displacing the inner C arm and the support such that the inner C arm and the support move in the same direction.

2. The X-ray stand according to claim 1, wherein the drive device is arranged in the support.

3. The X-ray stand according to claim 1, wherein
 the drive device actuates the inner C arm and the support via a first respectively second gear transmission ratio, and
 a ratio of the first and second gear transmission ratios equaling a ratio of the lengths of the outer and inner C arms.

4. The X-ray stand according to claim 1, further comprising a gear drive for implementing the first and second gear transmission ratios.

5. The X-ray stand according to claims 1, wherein
 the single drive unit is configured to displace the inner C arm using a first belt transmission and to drive a coupling wheel using a coupling transmission, the coupling wheel configured to displace the support using a second belt transmission,
 the ends of a belt of the first belt transmission are fastened to the inner C arm, and
 the ends of a belt of the second belt transmission are fastened to the outer C arm.

6. The X-ray stand according to claim 5, wherein the coupling transmission is a drive belt.

7. The X-ray stand according to claim 5, wherein the coupling transmission is a roller chain.

8. The X-ray stand according to claim 5, wherein the coupling transmission is a gear transmission.

9. The X-ray stand according to claim 1, wherein the outer C arm is rotatably connected to an arm of the X-ray stand using a shaft.

* * * * *